United States Patent [19]
Prasad et al.

[11] Patent Number: 6,147,221
[45] Date of Patent: Nov. 14, 2000

[54] PROCESS FOR THE MANUFACTURE OF SULFONYLAMINOCARBONYL TRIAZOLINONES AND SALTS THEREOF

[75] Inventors: Vidyanatha A. Prasad, Leawood; Shekhar V. Kulkarni, Shawnee; Eric Rivadeneira, Overland Park; Vijay C. Desai, Shawnee, all of Kans.

[73] Assignee: Bayer Corporation, Pittsburgh, Pa.

[21] Appl. No.: 09/472,335

[22] Filed: Dec. 27, 1999

[51] Int. Cl.[7] .................................................. C07D 249/12
[52] U.S. Cl. .......................................................... 548/263.4
[58] Field of Search .......................................... 548/263.4

[56] References Cited

U.S. PATENT DOCUMENTS

| | | | |
|---|---|---|---|
| 5,241,074 | 8/1993 | Daum et al. | 548/263.8 |
| 5,276,162 | 1/1994 | Muller et al. | 548/263.4 |
| 5,405,970 | 4/1995 | Daum et al. | 548/263.6 |
| 5,532,378 | 7/1996 | Daum et al. | 548/263.8 |
| 5,534,486 | 7/1996 | Müller et al. | 504/273 |
| 5,625,074 | 4/1997 | Daum et al. | 548/263.8 |
| 5,631,380 | 5/1997 | Haas et al. | 548/263.4 |
| 5,652,372 | 7/1997 | Muller et al. | 548/263.4 |
| 5,750,718 | 5/1998 | Müller et al. | 548/263.6 |
| 5,869,681 | 2/1999 | Müller et al. | 548/263.6 |

*Primary Examiner*—Patricia L. Morris
*Attorney, Agent, or Firm*—Joseph C. Gil

[57] ABSTRACT

The present invention relates to a process for manufacturing sulfonylaminocarbonyl triazolinones and salts thereof, which are herbicidally active compounds, wherein the process does not require isolation of the intermediate product. In particular, this invention relates to the conversion of a substituted triazolinone to a sulfonylaminocarbonyl triazolinone, and without the isolation of this intermediate product, the sulfonylaminocarbonyl triazolinone is then converted to a salt thereof.

14 Claims, No Drawings

PROCESS FOR THE MANUFACTURE OF SULFONYLAMINOCARBONYL TRIAZOLINONES AND SALTS THEREOF

TECHNICAL FIELD OF THE INVENTION

The present invention relates to a process for manufacturing sulfonylaminocarbonyl triazolinones and salts thereof, which are herbicidally active compounds, wherein the intermediate product of the process is not isolated. In particular, this invention relates to the conversion of a substituted triazolinone to a sulfonylaminocarbonyl triazolinone, and without the isolation of this intermediate product, the sulfonylaminocarbonyl triazolinone is then converted to a salt thereof.

In a preferred embodiment of the invention, 5-methoxy-4-methyl-2,4-dihydro-3H-1,2,4-triazol-3-one (MMT) is converted to 4,5-dihydro-3-methoxy-4-methyl-5-oxo-N-[[2-(trifluoromethoxy)phenyl]sulfonyl]-1H-1,2,4-triazole-1-carboxamide (MSU), and without isolating the MSU intermediate product, the MSU is converted to a salt thereof. Further, in another preferred embodiment of the invention, 5-propoxy-4-methyl-1,4-dihydro-3H-1,2,4-triazol-3-one (PMT) is converted to 2-[[[(4,5-dihydro-4-methyl-5-oxo-3-propoxy-1H-1,2,4-traizol-1-yl)carbonyl]amino]sulfonyl]-benzoic acid methyl ester (PSU), and without isolating the PSU intermediate product, the PSU is converted to a salt thereof.

BACKGROUND OF THE INVENTION

Sulfonylaminocarbonyl triazolinones are well known in the art, as are processes for their preparation and use as herbicides. European Patent EP-A 341,489 discloses certain substituted sulfonylaminocarbonyl triazolinones having herbicidal properties. Further, U.S. Pat. Nos. 5,534,486 and 5,869,681 describe a process for producing sulfonylaminocarbonyl triazolinones which are bonded by oxygen. The process includes the reaction of a triazolinone with a sulfonamide derivative. U.S. Pat. No. 5,750,718 describes intermediates for herbicidal sulfonylaminocarbonyl triazolinones having substituents which are bonded by sulfur.

However, the known prior art processes produce sulfonylaminocarbonyl triazolinones in unsatisfactory yield and purity. Thus, there is a need in the art for a process to manufacture sulfonylaminocarbonyl triazolinones in high yield and purity.

BRIEF SUMMARY OF INVENTION

The present invention is related to a process for the preparation of a sulfonylaminocarbonyl triazolinone or a salt thereof. The process includes the reaction of a substituted triazolinone of the following general formula (I)

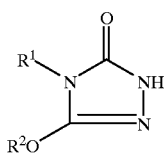

(I)

wherein
$R^1$ and $R^2$ each represents an unsubstituted or substituted alkyl, alkenyl, alkynyl, cycloalkyl, cycloalkylalkyl, aryl or arylalkyl radical, with a sulfonyl isocyanate of the following general formula (II)

$$O{=}C{=}N{-}SO_2{-}R^3 \qquad (II)$$

wherein
$R^3$ represents an unsubstituted or substituted alkyl, aryl, arylalkyl or heteroaryl radical, to produce a sulfonylaminocarbonyl triazolinone intermediate product of the general formula (III)

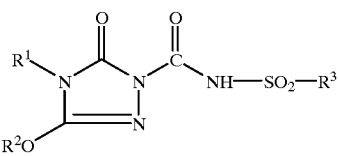

(III)

wherein $R^1$, $R^2$, and $R^3$ are as defined above.

The intermediate product is then reacted in a one pot process with a base to produce a salt thereof, a final product of the general formula (IV)

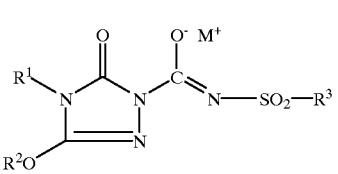

(IV)

wherein $R^1$, $R^2$, and $R^3$ are as defined above, and M represents an alkali or alkaline earth metal, or protonated ammonia derivative.

The process of the invention is carried out in a one pot process, without isolating or separating the intermediate product (formula III).

DETAILED DESCRIPTION OF THE INVENTION

The present invention is related to a process for the preparation of sulfonylaminocarbonyl triazolinones and salts thereof. The process includes the reaction of a substituted triazolinone of the following general formula (I)

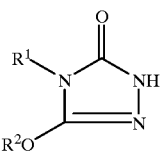

(I)

wherein
$R^1$ and $R^2$ each represents an unsubstituted or substituted alkyl, alkenyl, alkynyl, cycloalkyl, cycloalkylalkyl, aryl or arylalkyl radical, with a sulfonyl isocyanate of the following general formula (II)

$$O{=}C{=}N{-}SO_2{-}R^3 \qquad (II)$$

wherein
$R^3$ represents an unsubstituted or substituted alkyl, aryl, arylalkyl or heteroaryl radical, to produce a sulfonylaminocarbonyl triazolinone intermediate product of the general formula (III)

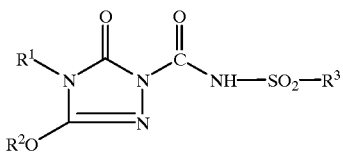

(III)

wherein $R^1$, $R^2$, and $R^3$ are as defined above.

Without isolation or separation, the intermediate product is then reacted with a base to produce a salt thereof, a final product of the general formula (IV)

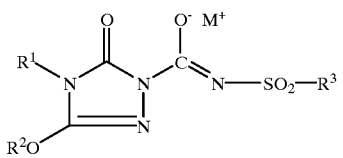

(IV)

wherein $R^1$, $R^2$, and $R^3$ are as defined above, and M represents an alkali or alkaline earth metal or protonated ammonia derivative.

The process of the invention is carried out in a one pot process, without isolating the intermediate product (formula II).

In a preferred embodiment of the invention, $R^1$ represents alkyl, alkenyl or alkynyl having in each case up to 6 carbon atoms, and each of which is unsubstituted or substituted by cyano, halogen, or $C_1$–$C_4$-alkoxy, or represents cycloalkyl group having 3 to 6 carbon atoms or cycloalkylalkyl group having 3 to 6 carbon atoms in the cycloalkyl moiety and 1 to 4 carbon atoms in the alkyl moiety, each of which is unsubstituted or substituted by halogen or $C_1$–$C_4$-alkyl, or represents aryl group having 6 or 10 carbon atoms or arylalkyl group having 6 or 10 carbon atoms in the aryl moiety and 1 to 4 carbon atoms in the alkyl moiety, each of which is unsubstituted or substituted by carboxyl, nitro, cyano, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl.

More preferably, $R^1$ represents methyl, ethyl, n- or i-propyl, n-, i-, s- or t-butyl, each of which is unsubstituted or substituted by cyano, fluorine, chlorine or bromine, methoxy or ethoxy, or represents propenyl, butenyl, propinyl or butinyl, each of which is unsubstituted or substituted by cyano, fluorine, chlorine or bromine, or represents cyclopropyl, cyclobutyl or cyclopropylmethyl, each of which is unsubstituted or substituted by fluorine, chlorine, bromine, methyl or ethyl, or represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl.

Most preferably, $R^1$ represents methyl.

In a preferred embodiment of the invention, $R^2$ represents alkyl, alkenyl or alkynyl, each of which has up to 6 carbon atoms, and each of which is unsubstituted or substituted by cyano, halogen or $C_1$–$C_4$-alkoxy, or represents cycloalkyl having 3 to 6 carbon atoms or cycloalkylalkyl having 3 to 6 carbon atoms in the cycloalkyl moiety and 1 to 4 carbon atoms in the alkyl moiety, each of which is unsubstituted or substituted by halogen or $C_1$–$C_4$-alkyl, or represents aryl having 6 to 10 carbon atoms or arylalkyl having 6 or 10 carbon atoms in the aryl moiety and 1 to 4 carbon atoms in the alkyl moiety, each of which is unsubstituted or substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl.

More preferably, $R^2$ represents methyl, ethyl, n- or i-propyl or n-, i-, s- or t-butyl, each of which is unsubstituted or substituted by cyano, fluorine, chlorine or bromine, methoxy or ethoxy, or represents propenyl, butenyl, propinyl or butinyl, each of which is unsubstituted or substituted by cyano, fluorine, chlorine or bromine, or represents cyclopropyl, or cyclopropylmethyl, each of which is unsubstituted or substituted by fluorine, chlorine, bromine, methyl or ethyl, or represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl.

Most preferably, $R^2$ represents methyl, n- or i-propyl.

In a preferred embodiment of the invention, $R^3$ represents the group

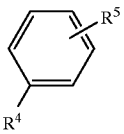

wherein $R^4$ and $R^5$ are identical or different and represent hydrogen, fluorine, chlorine, bromine, iodine, nitro, $C_1$–$C_6$-alkyl, which is unsubstituted or substituted by fluorine, chlorine, bromine, cyano, carboxyl, $C_1$–$C_4$-alkoxycarbonyl, $C_1$–$C_4$-alkylaminocarbonyl, di-($C_1$–$C_4$-alkyl)aminocarbonyl, hydroxyl, $C_1$–$C_4$-alkoxy, formyloxy, $C_1$–$C_4$-alkylcarbonyloxy, $C_1$–$C_4$-alkoxycarbonyloxy, $C_1$–$C_4$-alkylaminocarbonyloxy, $C_1$–$C_4$-alkylthio, $C_1$–$C_4$-alkylsulfinyl, $C_1$–$C_4$-alkylsulfonyl, di-($C_1$–$C_4$-alkyl)-aminosulfonyl, $C_3$–$C_6$-cycloalkyl or phenyl, or represent $C_2$–$C_6$-alkenyl which is unsubstituted or substituted by fluorine, chlorine, bromine, cyano, $C_1$–$C_4$-alkoxycarbonyl, carboxyl or phenyl, or represent $C_2$–$C_6$-alkynyl which is unsubstituted or substituted by fluorine, chlorine, bromine, cyano, $C_1$–$C_4$-alkoxycarbonyl, carboxyl or phenyl, or represent $C_1$–$C_4$-alkoxy which is unsubstituted or substituted by fluorine, chlorine, bromine, cyano, carboxyl, $C_1$–$C_4$-alkoxycarbonyl, $C_1$–$C_4$-alkoxy, $C_1$–$C_4$-alkylthio, $C_1$–$C_4$-alkylsulfinyl or $C_1$–$C_4$-alkylsulfonyl, or represent $C_1$–$C_4$-alkylthio which is unsubstituted or substituted by fluorine, chlorine, bromine, cyano, carboxyl, $C_1$–$C_4$-alkoxycarbonyl, $C_1$–$C_4$-alkylthio, $C_1$–$C_4$-alkylsulfinyl or $C_1$–$C_4$-alkylsulfonyl, or represent $C_3$–$C_6$ alkenyloxy which is unsubstituted or substituted by fluorine, chlorine, bromine, cyano or $C_1$–$C_4$-alkoxycarbonyl, or represent $C_2$–$C_6$-alkenylthio which is unsubstituted or substituted by fluorine, chlorine, bromine, cyano, nitro, $C_1$–$C_3$-aklylthio or $C_1$–$C_4$-alkoxycarbonyl, $C_3$–$C_6$-alkynyloxy, $C_3$–$C_6$-alkynylthio or the radical —S(O)$_p$—$R^6$ where p represents the numbers 1 or 2, and $R^6$ represents $C_1$–$C_4$-alkyl which is unsubstituted or substituted by fluorine, chlorine, bromine, cyano or $C_1$–$C_4$-alkoxycarbonyl, $C_3$–$C_6$-alkenyl, $C_3$–$C_6$-alkynyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)amino, phenyl or the radical —NHOR$^7$ wherein $R^7$ represents $C_1$–$C_{12}$-alkyl which is unsubstituted or substituted by fluorine, chlorine, cyano, $C_1$–$C_4$-alkoxy, $C_1$–$C_4$-alkylthio, $C_1$–$C_4$-alkylsulfinyl, $C_1$–$C_4$-alkylsulfonyl, $C_1$–$C_4$-alkyl-carbonyl, $C_1$–$C_4$-alkoxycarbonyl, $C_1$–$C_4$-alkylaminocarbonyl or di-($C_1$–$C_4$-alkyl)-amino-carbonyl), or represents $C_3$–$C_6$-alkenyl which is unsubstituted or substituted by fluorine, chlorine or bromine, $C_3$–$C_8$-alkynyl, $C_3$–$C_8$-cycloalkyl, $C_3$–$C_6$-cycloalkyl-$C_1$–$C_2$-alkyl, phenyl-$C_1$–$C_2$-alkyl which is unsubstituted or substituted by fluorine, chlorine, nitro, cyano, $C_1$–$C_4$-alkyl, $C_1$–$C_4$-alkoxy or $C_1$–$C_4$-alkoxycarbonyl), or represents benzhydryl, or represents phenyl which is unsubstituted or substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxycarbonyl, $R^4$ and/or $R^5$ furthermore represent phenyl or phenoxy, or represent $C_1$–$C_4$-alkylcarbonylamino, $C_1$–$C_4$-alkoxycarbonylamino, $C_1$–$C_4$-alkylamino-carbonyl-amino, di-($C_1$–$C_4$-alkyl)amino-carbonyl-amino, or the radical —CO—$R^8$ wherein $R^8$ represents $C_1$–$C_6$-alkyl, $C_1$–$C_6$-alkoxy, $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino which are unsubstituted or substituted by halogen selected from the group consisting of fluorine and chlorine, p1 $R^4$ and/or $R^5$ furthermore represent trimethylsilyl, thiazolinyl, $C_1$–$C_4$-alkylsulfonyloxy, di-($C_1$–$C_4$-alkyl)-aminosulfonylamino or the radical —CH=N—$R^9$ wherein $R^9$ represents $C_1$–$C_6$-alkyl which is unsubstituted or substituted by fluorine, chlorine, cyano, carboxyl, $C_1$–$C_4$-alkoxy, $C_1$–$C_4$-alkylthio, $C_1$–$C_4$-alkylsulfinyl or $C_1$–$C_4$-alkylsulfonyl, or represents benzyl which is unsubstituted or substituted by fluorine or chlorine, or represents $C_3$–$C_6$-alkenyl or $C_3$–$C_6$-alkynyl, each of which is unsubstituted or substituted by fluorine or chlorine, or represents phenyl which is unsubstituted or substituted by fluorine, chlorine, bromine, $C_1$–$C_4$-alkyl, $C_1$–$C_4$-alkoxy, trifluoromethyl, trifluoromethoxy or trifluoromethylthio, or represents unsubstituted or halogen substituted $C_1$–$C_6$-alkoxy, $C_3$–$C_6$-alkenoxy, $C_3$–$C_6$-alkynoxy or benzyloxy, wherein the halogen is selected from the group consisting of fluorine and chlorine, or represents amino, $C_1$–$C_4$-alkylamino, di-($C_1$–$C_4$-alkyl)-amino, phenylamino, $C_1$–$C_4$-alkyl-carbonylamino, $C_1$–$C_4$-alkoxycarbonylamino or $C_1$–$C_4$-alkyl-sulfonylamino, or represents phenylsulfonylamino which is unsubstituted or substituted by fluorine, chlorine, bromine or methyl, furthermore $R^3$ represents the radical

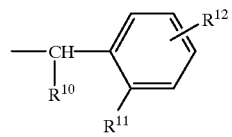

wherein $R^{10}$ represents hydrogen or $C_1$–$C_4$-alkyl, $R^{11}$ and $R^{12}$ are identical or different and represent hydrogen, fluorine, chlorine, bromine, nitro, cyano, $C_1$–$C_4$-alkyl which is unsubstituted or substituted by halogen selected from the group consisting of fluorine and chlorine, $C_1$–$C_4$-alkoxy which is unsubstituted or substituted by halogen selected from the group consisting of fluorine and chlorine, carboxyl, $C_1$–$C_4$-alkoxy-carbonyl, dimethylaminocarbonyl, $C_1$–$C_4$-alkylsulfonyl or di-($C_1$–$C_4$-alkyl)-aminosulfonyl;

furthermore $R^3$ represents the radical

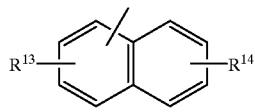

wherein $R^{13}$ and $R^{14}$ are identical or different and represent hydrogen, fluorine, chlorine, bromine, nitro, cyano, $C_1$–$C_4$-alkyl which is unsubstituted or substituted by halogen selected from the group consisting of fluorine and chlorine, or $C_1$–$C_4$-alkoxy which is unsubstituted or substituted by halogen selected from the group consisting of fluorine and chlorine;

furthermore $R^3$ represents the radical

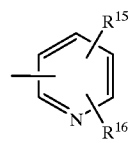

wherein $R^{15}$ and $R^{16}$ are identical or different and represent hydrogen, fluorine, chlorine, bromine, nitro, cyano, $C_1$–$C_4$-alkyl which is unsubstituted or substituted by halogen selected from the group consisting of fluorine and chlorine, $C_1$–$C_4$-alkoxy which is unsubstituted or substituted by halogen selected from the group consisting of fluorine and chlorine, or represent $C_1$–$C_4$-alkylthio, $C_1$–$C_4$-alkylsulfinyl or $C_1$–$C_4$-alkylsulfonyl which are unsubstituted or substituted by halogen selected from the group consisting of fluorine and chlorine, or represent aminosulfonyl, mono-($C_1$–$C_4$-alkyl)aminosulfonyl, di-($C_1$–$C_4$-alkyl)-aminosulfonyl or $C_1$–$C_4$-alkoxycarbonyl or dimethylaminocarbonyl;

furthermore $R^3$ represents the radical

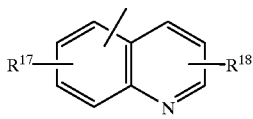

wherein $R^{17}$ and $R^{18}$ are identical or different and represent hydrogen, fluorine, chlorine, bromine, $C_1$–$C_4$-alkyl which is unsubstituted or substituted by halogen selected from the group consisting of fluorine and bromine, $C_1$–$C_4$-alkoxy which is unsubstituted or substituted by halogen selected from the group consisting of fluorine and chlorine, $C_1$–$C_4$-alkylthio, $C_1$–$C_4$-alkylsulfinyl or $C_1$–$C_4$-alkylsulfonyl which are unsubstituted or substituted by halogen selected from the group consisting of fluorine and chlorine, or represent di-($C_1$–$C_4$-alkyl)-aminosulphonyl;

furthermore $R^3$ represents the radical

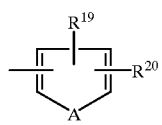

wherein $R^{19}$ and $R^{20}$ are identical or different and represent hydrogen, fluorine, chlorine, bromine, cyano, nitro, $C_1$–$C_4$-alkyl which is unsubstituted or substituted by halogen selected from the group consisting of fluorine and chlorine, $C_1$–$C_4$-alkoxy which is unsubstituted or substituted by halogen selected from the group consisting of fluorine and chlorine, $C_1$–$C_4$-alkylthio, $C_1$–$C_4$-alkylsulfinyl or $C_1$–$C_4$-alkylsulfinyl which is unsubstituted or substituted by halogen selected from the group consisting of fluorine and chlorine, di-($C_1$–$C_4$-alkyl)aminosulfonyl, $C_1$–$C_4$-alkoxy-carbonyl or dimethylaminocarbonyl, and A represents oxygen, sulfur or the group N—$Z^1$, wherein $Z^1$ represents hydrogen, $C_1$–$C_4$-alkyl which is unsubstituted or substituted by fluorine, chlorine, bromine, or cyano, $C_3$–$C_6$-cycloalkyl, benzyl, phenyl which is unsubstituted or substituted by fluorine, chlorine, bromine or nitro, $C_1$–$C_4$-alkylcarbonyl, $C_1$–$C_4$-alkoxycarbonyl or di-($C_1$–$C_4$-alkyl)amino-carbonyl;

furthermore $R^3$ represents the radical

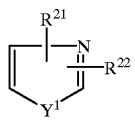

wherein $R^{21}$ and $R^{22}$ are identical or different and represent hydrogen, $C_1$–$C_4$-alkyl, halogen, $C_1$–$C_4$-alkoxycarbonyl, $C_1$–$C_4$-alkoxy or $C_1$–$C_4$-halogenoalkoxy, $Y^1$ represents sulfur or the group N—$R^{23}$, wherein $R^{23}$ represents hydrogen or $C_1$–$C_4$-alkyl;

furthermore $R^3$ represents the radical

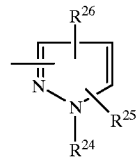

wherein $R^{24}$ represents hydrogen, $C_1$–$C_4$-alkyl, benzyl, pyridyl, quinolinyl or phenyl, $R^{25}$ represents hydrogen, halogen, cyano, nitro, $C_1$–$C_4$-alkyl which is unsubstituted or substituted by halogen selected from the group consisting of fluorine and chlorine, $C_1$–$C_4$-alkoxy which is unsubstituted or substituted by halogen selected from the group consisting of fluorine and chlorine, dioxolanyl or $C_1$–$C_4$-alkoxycarbonyl, and $R^{26}$ represents hydrogen, halogen or $C_1$–$C_4$-alkyl;

furthermore $R^3$ represents a compound selected from the group consisting of

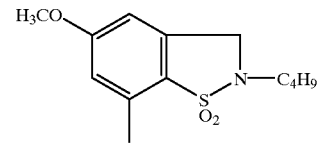

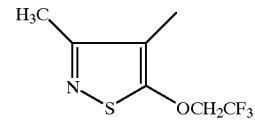

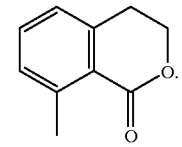

The invention furthermore preferably relates to the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, $C_5$- or $C_6$-cycloalkyl-ammonium and di-($C_1$–$C_2$-alkyl)-benzyl-ammonium salts of the formula (IV) in which $R^1$, $R^2$ and $R^3$ have the meanings mentioned above as being preferred.

In particular, the invention relates to compounds of the formula (IV)

wherein $R^1$ represents hydrogen, amino, $C_1$–$C_4$-alkyl which is unsubstituted or substituted by fluorine, cyano, methoxy or ethoxy, or represents allyl, $C_3$–$C_6$-cycloalkyl, benzyl, phenyl, $C_1$–$C_3$-alkylamino, $C_3$–$C_6$-cycloalkylamino or di-($C_1$–$C_3$-alkyl)-amino, $R^2$ represents $C_1$–$C_4$-alkyl which is unsubstituted or substituted by halogen selected from the group consisting of fluorine and/or chlorine, methoxy or ethoxy, or represents $C_3$–$C_4$-alkenyl which is optionally substituted by fluorine and chlorine, or represents $C_3$–$C_6$-cycloalkyl, or represents benzyl which is unsubstituted or substituted by a compound selected from the group consisting of fluorine, chlorine and methyl, and $R^3$ represents the group

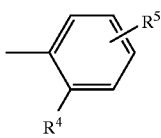

wherein $R^4$ represents fluorine, chlorine, bromine, methyl, trifluoromethyl, methoxy, difluoromethoxy, trifluoromethoxy, 2-chloro-ethoxy, 2-methoxy-ethoxy, $C_1$–$C_3$-alkylthio, $C_1$–$C_3$-alkysulfinyl, $C_1$–$C_3$-alkylsulfonyl, dimethylaminosulfonyl, diethylaminosulfonyl, N-methoxy-N-methylaminosulfonyl, methoxyaminosulfonyl, phenyl, phenoxy or $C_1$–$C_3$-alkoxycarbonyl and $R^5$ represents hydrogen, fluorine, chlorine or bromine; furthermore $R^3$ represents the radical

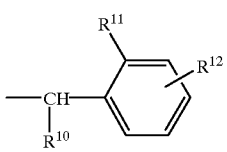

wherein $R^{10}$ represents hydrogen, $R^{11}$ represents fluorine, chlorine, bromine, methyl, methoxy, difluoromethoxy, trifluorormethoxy, ethoxy, methoxycarbonyl, ethoxycarbonyl, methylsulfonyl or dimethylaminosulfonyl, and $R^{12}$ represents hydrogen; furthermore $R^3$ represents the radical

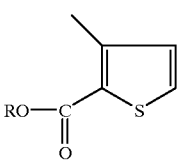

wherein

R represents $C_1$–$C_4$-alkyl, or represents the radical

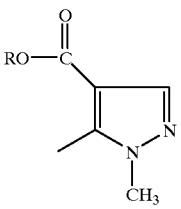

wherein

R represents $C_1$–$C_4$-alkyl.

The process of the invention is conducted as a one pot process, without isolating or separating the intermediate product of formula (III).

The process according to the invention is generally carried out at atmospheric pressure. However, it is also possible to conduct the process under elevated or reduced pressure.

The reaction of the substituted triazolinone (formula I) with the sulfonyl isocyanate (formula II) to produce the sulfonylaminocarbonyl triazolinone intermediate product (formula III), is carried out at a temperature of from about −20° C. to about 120° C., and preferably at a temperature of from about 0° C. to about 45° C.

The reaction time to produce the intermediate product is up to about 48 hours, and preferably from about 1 hour to about 8 hours.

In the process of the invention, suitable sulfonyl isocyanates include 2-(trifluoromethoxy) benzensulfonyl isocyanate, 2-(methoxycarbonyl)benzenesulfonyl isocyanate, benzenesulfonyl isocyanate, p-toluenesulfonyl isocyanate, 2-fluoro, 2-chloro-, 2-bromo-, 2-methyl-, 2-methoxy-, 2-trifluoromethyl-, 2-difluoro-methoxy-, 2-trifluoromethoxy-, 2-methylthio-, 2-ethylthio-, 2-propylthio-, 2-methylsulfinyl-, 2-methyl-sulfonyl-, 2-dimethylaminosulfonyl-, 2-diethylaminosulfonyl-, 2-(N-methoxy-N-methyl-aminosulfonyl-, 2-phenyl-, 2-phenoxy-, 2-methoxycarbonyl-, 2-ethoxycarbonyl, 2-propoxycarbonyl- and 2-isopropoxycarbonyl-phenylsulfonyl isocyanate, 2-fluoro-, 2-chloro-, 2-difluoromethoxy-, 2-trifluoromethoxy-, 2-methoxycarbonyl- and 2-ethoxycarbonyl-benzylsulfonyl isocyanate, 2-methoxycarbonyl-3-thienylsulfonyl isocyanate, 4-methoxycarbonyl- and 4-ethoxy-carbonyl-1-methyl-pyrazol-5-yl-sulfonyl isocyanate.

In a preferred embodiment, the sulfonyl isocyanate is 2-(trifluoromethoxy)benzenesulfonyl isocyanate or 2-(methoxycarbonyl)benzenesulfonyl isocyanate.

In an embodiment of the invention, the reaction of the substituted triazolinone (formula I) with the sulfonyl isocyanate (formula II) is carried out in the presence of a solvent. Suitable solvents include inert organic solvents such as aliphatic and aromatic, unhalogenated or halogenated hydrocarbons such as pentane, hexane, heptane, cyclohexane, methylene chloride, ethylene chloride, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dibutyl ether, dioxane, tetrahydrofuran or diglycol dimethyl ether, glycol dimethyl ether or ethylene glycol diethyl ether; ketones such as acetone, butanone, methyl ethyl ketone, methyl isopropyl ketone or methyl isobutyl ketone; nitriles such as acetonitrile, propionitrile or butyronitrile; amides such as N,N-dimethylformamide, N,N-dimethylacetamide, N-methyl-formanilide, N-methyl-pyrrolidone or hexamethylphosphoric triamide; esters such as methyl acetate or ethyl acetate; also dimethyl sulfoxide, tetramethylene sufone and hexamethylphosphoric triamide.

Preferably, the solvent used in the process of the invention is methyl isobutyl ketone, or xylene, or a commercially available mixture of xylenes containing ortho-xylene, para-xylene and meta-xylene.

The reaction of a sulfonylaminocarbonyl triazolinone intermediate product (formula III) with a base, to convert the intermediate product to a salt thereof (the final product of formula IV), is carried out without isolation or separation of the intermediate product. This reaction of the intermediate product with the base is carried out at a temperature of from about −20° C. to about 120° C., and preferably from about 0° C. to about 45° C.

The reaction time to convert the intermediate product to the final product is up to about 48 hours, and preferably from about 2 hours to about 8 hours.

During this conversion step of the sulfonylaminocarbonyl triazolinone intermediate product (formula III) to a salt thereof (final product of the formula IV), the addition of the base is continued until the conversion is complete.

Suitable bases for this conversion step include bases such as alkaline and alkali earth metals, hydroxides, alkoxides, bicarbonates, carboxylates, amines, ammonia, and aqueous mixtures thereof. Preferably, the base that is used in the process of the invention is sodium hydroxide, sodium methylate, sodium ethylate, potassium hydroxide, potassium methylate or potassium ethylate, isopropylamine, dibutylamine or triethylamine, or aqueous mixtures thereof. More preferably, the base is sodium hydroxide, or an aqueous solution of sodium hydroxide.

In an embodiment of the invention, the conversion of the intermediate product (formula III) to the final product (formula IV) is carried out in the presence of a solvent. Suitable solvents include aliphatic, alicyclic or aromatic, unhalogenated or halogenated hydrocarbons such as benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran or ethylene glycol dimethyl ether or ethylene glycol diethyl ether; ketones such as acetone, butanone, or methyl iosbutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate, sulphoxides such as dimethyl sulphoxide, alcohols such as methanol, ethanol, n- or i-propanol, n-, i-, s-, or t-butanol, ethylene glycol monomethyl ether, ethylene glycol monoethyl ether, diethylene glycol monomethyl ether, diethylene glycol monoethyl ether; water and mixtures thereof. Preferred solvents include water, methyl isobutyl ketone, propanol, methanol, toluene, a commercially available mixture of xylenes containing ethylbenzene, ortho-xylene, para-xylene, metaxylene, and mixtures thereof.

In a preferred embodiment of this invention, the conversion of the intermediate product (formula III) to the final product (formula IV) is carried out in a mixture of water and methyl isobutyl ketone, or a mixture of water, methyl isobutyl ketone and xylenes.

In a preferred embodiment of the invention, 5-methoxy-4-methyl-2,4-dihydro-3H-1,2,4-triazol-3-one (MMT) is converted to 4,5-dihydro-3-methoxy-4-methyl-5-oxo-N-[[2-(trifluoromethoxy)phenyl]sulfonyl]-1H-1,2,4-triazole-1-carboxamide (MSU), and without isolating the MSU intermediate product, the MSU is converted to a salt thereof. Further, in another preferred embodiment of the invention, 5-propoxy-4-methyl-1,4-dihydro-3H-1,2,4-triazol-3-one (PMT) is converted to 2-[[[(4,5-dihydro-4-methyl-5-oxo-3-propoxy-1H-1,2,4-traizol-1-yl)carbonyl]amino]sulfonyl] benzoic acid methyl ester (PSU), and without isolating the PSU intermediate product, the PSU is converted to a salt thereof.

In another embodiment of the invention, the salt of the MSU is isolated as a monohydrate.

The invention is further illustrated but is not intended to be limited by the following examples in which all parts and percentages are by weight unless otherwise specified.

EXAMPLES

Example 1

The Preparation of MKH 6562 Hydrate

About 261.0 grams (1.74 moles) of 98% pure 5-methoxy-4-methyl-2,4-dihydro-3H-1,2,4-triazol-3-one (MMT) hydrate in about 2600 grams of methyl isobutyl ketone (MIBK) were dried by azeotropic distillation of part of the MIBK under reduced pressure (with a pot temperature of about 80° C.), and then cooled to room temperature under a nitrogen atmosphere. To the resulting MMT slurry in MIBK was added about 534.0 grams (1.74 moles) of 87% pure 2-(trifluoromethoxy) benzenesulfonyl isocyanate over a period of about 2 hours. The reaction mixture was stirred at room temperature for about 6 hours. The conversion reaction of the MMT was monitored using a liquid chromatograph. About 140.0 grams of water were added to the reaction mixture. The mixture was then treated with 50% aqueous sodium hydroxide (NaOH) until the reaction was complete. The reaction mixture was stirred for about 1 hour, filtered, washed with about 500 grams of MIBK and dried to isolate the MKH 6562 hydrate. The yield of MKH 6562 hydrate was 719.9 grams (i.e., 93% yield based on MMT hydrate) and the purity was 98% (as hydrate).

Example 2

The Preparation of MKH 6561

To a solution (dried by azeotropic distillation) containing 62.8 grams (0.40 moles) of 5-propoxy-4-methyl-2,4-dihydro-3H-1,2,4-triazol-3-one (PMT) in about 250 grams of methyl isobutyl ketone (MIBK) was added a solution of 160.8 grams (0.40 moles) of 60% pure 2-methoxycarbonylbenzenesulfonyl isocyanate in 80 grams of MIBK at a temperature of from about 30° C. to about 32° C., over a time period of about 2 hours.

After the addition was complete, the reaction mixture was allowed to come to room temperature and the mixture was stirred for about 16 hours to complete the formation of PSU.

To convert the PSU to MKH 6561, the reaction mixture was diluted with 10 grams of water and then treated with 50% aqueous NaOH solution over a period of about 6 hours, until all the PSU was converted into its sodium salt, i.e., MKH 6561.

To isolate the product, the reaction mixture was filtered under vacuum, washed twice with 400 grams of warm (45° C.) MIBK and dried under vacuum at room temperature to give 160.8 grams (87% pure) MKH 6561. The net isolated yield based on PMT was 83.3%.

The purity of the isolated MKH 6561 was only 87% mainly because the isocyanate contained about 15–20% of 2-methoxycarbonylbenzenesulfonyl chloride as impurity. Some of this hydrolyzed under the reaction conditions to the corresponding sulfonic acid which then formed the sodium salt and ended up in the product.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a sulfonylaminocarbonyl triazolinone or a salt thereof, comprising the steps of:

a) reacting a substituted triazolinone of the following general formula (I)

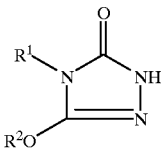

(I)

wherein

R¹ and R² each represents an unsubstituted or substituted alkyl, alkenyl, alkynyl, cycloalkyl, cycloalkylalkyl, aryl or arylalkyl radical, with a sulfonyl isocyanate of the following general formula (II)

(II)

wherein

R³ represents an unsubstituted or substituted alkyl, aryl, arylalkyl or heteroaryl radical, to produce a sulfonylaminocarbonyl triazolinone intermediate product of the general formula (III)

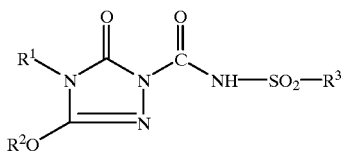

(III)

wherein R¹, R², and R³ are as defined above, and b) reacting the intermediate product, in a one pot process with a base to produce a salt thereof, a final product of the general formula (IV)

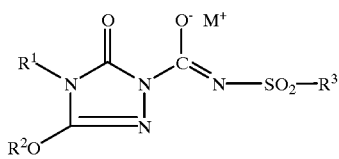

(IV)

wherein R¹, R², and R³ are as defined above, and M represents an alkali or alkaline earth metal, or protonated ammonia derivative.

2. The process of claim 1 wherein the reaction in steps a) and b) is carried out at a temperature of from about −20° C. to about 120° C.

3. The process of claim 1 wherein the reaction in steps a) and b) is carried out at a temperature of from about 0° C. to about 45° C.

4. The process of claim 1 wherein the reaction in step a) is carried out in the presence of a solvent.

5. The process of claim 4 wherein the solvent is selected from the group consisting of aliphatic and aromatic unhalogenated or halogenated hydrocarbons, ethers, ketones, nitrites, amides, esters, dimethyl sulfoxide, tetramethylene sulfone and hexamethylphosphoric triamide.

6. The process of claim 1 wherein the sulfonyl isocyanate is selected from the group consisting of 2-(trifluoromethoxy) benzenesulfonyl isocyanate or 2-(methoxycarbonyl) benzenesulfonyl isocyanate.

7. The process of claim 1 wherein the base recited in step b) is selected from the group consisting of alkaline and alkali earth metals, hydroxides, alkoxides, bicarbonates, carboxylates, amines, ammonia, and aqueous mixtures thereof.

8. The process of claim 7 wherein the base is selected from the group consisting of sodium hydroxide, sodium methylate, sodium ethylate, potassium hydroxide, potassium methylate, potassium ethylate, isopropylamine, dibutylamine, triethylamine, and aqueous mixtures thereof.

9. The process of claim 1 wherein the reaction in step b) is carried out in the presence of a solvent.

10. The process of claim 9 wherein the solvent is selected from the group consisting of aliphatic, alicyclic and aromatic, unhalogenated or halogenated hydrocarbons, ethers, ketones, nitriles, amides, esters, alcohols, water and mixtures thereof.

11. The process of claim 9 wherein the solvent is a mixture of methyl isobutyl ketone and water.

12. The process of claim 9 wherein the solvent is a mixture of xylenes, methyl isobutyl ketone and water.

13. The process of claim 1 wherein 5-methoxy-4-methyl-2,4-dihydro-3H-1,2,4-triazol-3-one (MMT) is converted to 4,5-dihydro-3-methoxy-4-methyl-5-oxo-N-[[2-(trifluoromethoxy)phenyl]sulfonyl]-1H-1,2,4-triazole-1-carboxamide (MSU), and the MSU is converted to a salt thereof.

14. The process of claim 13 further comprising the step of isolating the MSU salt thereof as a monohydrate.

* * * * *